United States Patent [19]

Kamon

[11] Patent Number: 5,073,918
[45] Date of Patent: Dec. 17, 1991

[54] ANGLE DETECTOR DEVICE FOR SILICON WAFERS

[75] Inventor: Kazuya Kamon, Itami, Japan

[73] Assignee: Mitsubishi Denki Kabushiki Kaisha, Japan

[21] Appl. No.: 564,163

[22] Filed: Aug. 8, 1990

[30] Foreign Application Priority Data

Feb. 13, 1990 [JP] Japan ................................. 2-32809

[51] Int. Cl.$^5$ .............................................. A61B 6/08
[52] U.S. Cl. .................................. 378/205; 378/34; 378/35; 378/70; 378/71
[58] Field of Search .................. 378/73, 70, 71, 72, 378/86, 62, 87, 74, 34, 35, 205, 68

[56] References Cited

U.S. PATENT DOCUMENTS 4,412,345 10/1983 Workman et al. .................. 378/78

Primary Examiner—Edward P. Westin
Assistant Examiner—Don Wong
Attorney, Agent, or Firm—Leydig, Voit & Mayer

[57] ABSTRACT

An angle detector for determining the orientation of the crystal axes of silicon wafers is disclosed. A portion of an X-ray beam generated by a synchrotron for exposing a wafer is directed onto the back surface of the wafer via a pair of monocrystalline silicon plate diffraction gratings and a slit having a pin-hole for collimating the X-ray. The X-ray beams diffracted by the wafer form a diffraction pattern on a two-dimensional photosensor array, from which pattern the angular position of the wafer is determined. The angle is determined by an image processor, a memory for storing a diffraction pattern corresponding to a predetermined angular position of the wafer, and a comparison of the image processor output and the memory data.

7 Claims, 3 Drawing Sheets

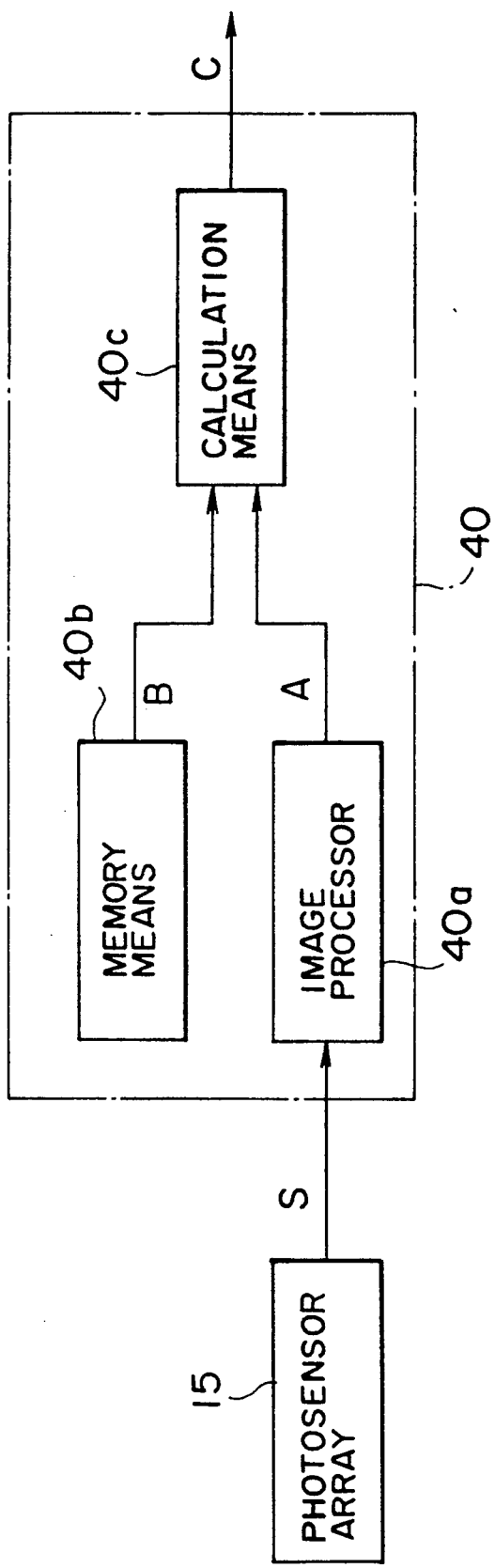
F I G. 4

ANGLE DETECTOR DEVICE FOR SILICON WAFERS

BACKGROUND OF THE INVENTION

This invention relates to an angle detector device for detecting the angular position or orientation of a semiconductor wafer, and especially to an angle detector device for a precise determination of the angular position of a silicon wafer with respect to the crystal axes thereof in a photolithography step in the LSI production process.

In the production of LSI's, etc., fine patterns are formed on silicon wafers by means of photolithography. Before the photoresist on the wafer is exposed in the photolithography process, the angular position of the wafer must be determined and adjusted so that the photolithography exposure pattern is aligned with the crystal axes of the wafer.

Referring first to FIG. 1, let us describe a conventional method for determining the angular position of a silicon wafer 30 around its central axis. A disk-shaped silicon wafer 30 is supported on a holder (not shown) rotatable in the direction 31. The determination of the angular position of the wafer 30 is effected by means of a flat surface 32 (referred to hereinafter as orientational flat) formed on the edge of the wafer. A laser oscillator 33 generates a laser beam 34 directed toward a peripheral portion of wafer 30. The wafer 30 is rotated while the laser beam 34 irradiates on the edge of the wafer 33. The laser beam 34 is transmitted through the edge of the wafer 30 and hence is received by a photosensor 35 opposing the laser oscillator 33 only when the wafer 30 is at such a rotational position that the laser beam 34 falls on the orientational flat 32. Thus, the angular position of the wafer 30 can be determined and adjusted on the basis of the profile of the output signal of the photosensor 35.

The above method of detecting the angular position of silicon wafers, however, has the following disadvantage. Namely, according to the above conventional method, the determination of the directions of the crystal axes of the wafer is effected only indirectly by means of the orientational flat 32. Thus precise alignment of the crystal axes of the wafer to the photolithography pattern is hard to effect. In addition, the precision of the angular position of the wafer in the photolithography step is further reduced due to the fact that the wafer may be moved a number of times after the angle thereof is set.

SUMMARY OF THE INVENTION

It is therefore a primary object of this invention to provide an angle detector device for detecting the angular position of crystalline semiconductor wafers by directly determining the directions of the crystal axes of the wafer such that the reticle of the photolithography exposure device can be aligned precisely with the crystal axes of the wafer. In addition, this invention provides an angle detector device for enhancing the precision of the angular setting of the wafer in the photolithography process.

The above objects are accomplished according to the principle of this invention by an angle detector device which comprises: X-ray irradiation means for generating an X-ray beam which is directed onto the wafer and diffracted thereby sensor means for detecting a Laue diffraction pattern formed by the X-rays diffracted by the wafer; and angle determination means, coupled to the output of the sensor means, for determining the angular position of the wafer on the basis of the Laue diffraction pattern detected by the sensor means.

Preferably, the sensor means comprises a two-dimensional photosensor array for detecting the Laue diffraction pattern, and the angle determination means comprises image processing means, coupled to an output of the photosensor array, for generating an output corresponding to the Laue diffraction pattern detected by the photosensor array; memory means for storing a Laue diffraction pattern corresponding to a predetermined angular position of the wafer; and calculation means, coupled to the image processing means and the memory means, for determining the deviation of the detected Laue diffraction pattern from the stored Laue diffraction pattern, the calculation means thereby determining the angular position of the wafer with respect to crystal axes thereof.

The precise alignement of the crystal axes of the wafer with the photolithography exposure pattern is particularly important in the case of the newly developed semiconductor devices in which quatum effects come into play. The angle detector device according to this invention is especially suited for the precise determination of the angular position of a wafer that is required in the production of such semiconductor devices.

BRIEF DESCRIPTION OF THE DRAWINGS

The novel features which are believed to be characteristic of this invention are set forth with particularity in the appended claims. This invention itself, however, both as to its organization and method of operation, together with further objects and advantages thereof, may best be understood by reference to the following detailed description, taken in connection with the accompanying drawings, in which:

FIG. 4 is a block diagram showing an implementation of the angle determination means according to this invention.

In the drawings, like reference numerals represent like or corresponding parts or portions.

DETAIELD DESCRIPTION OF THE PREFERRED EMBODIMENT

Figure 2:
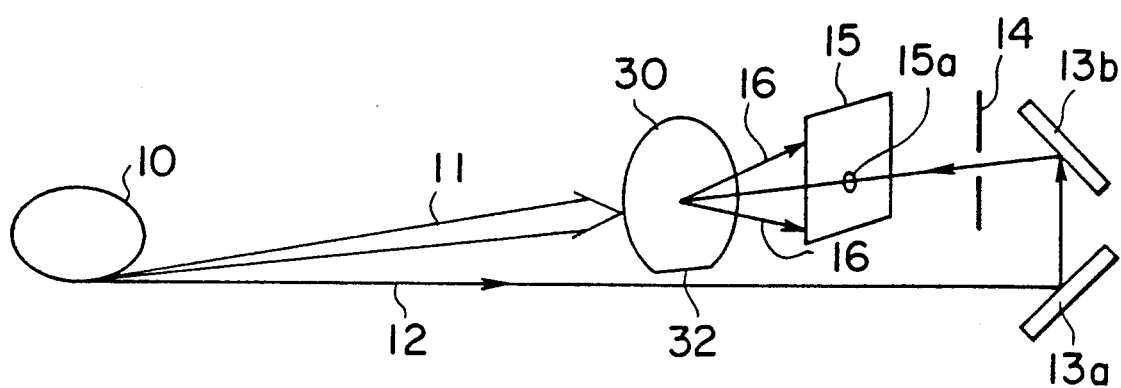
FIG. 2 is a schematic view of an angle detector device for silicon wafers according to this invention.
Figure 3:
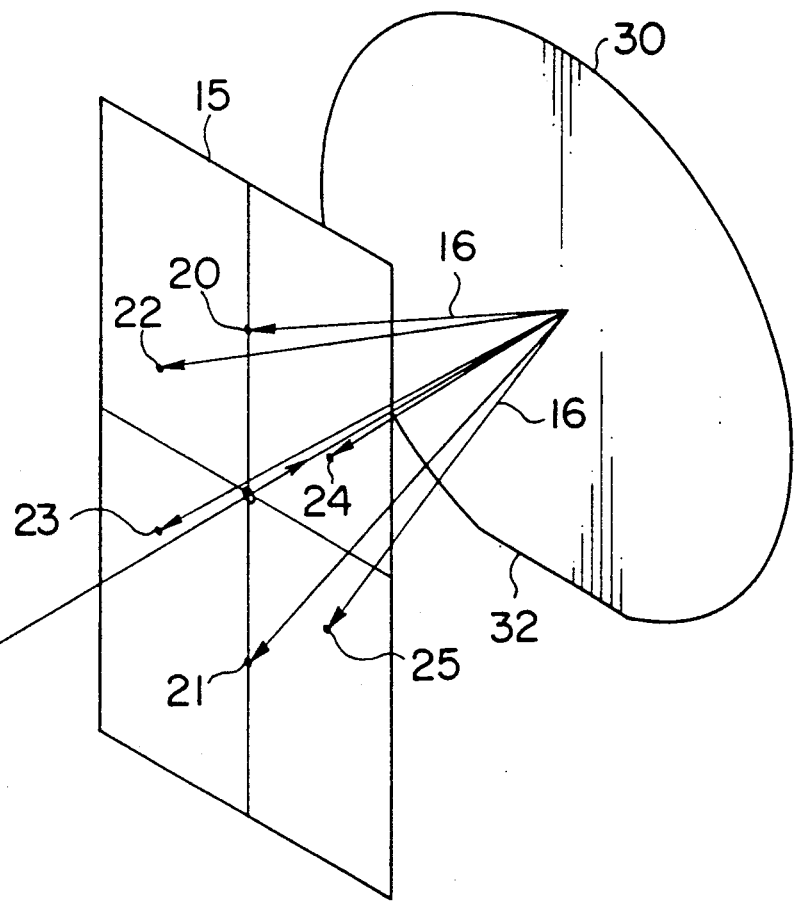
FIG. 3 is a schematic perspective view of a two-dimensional photosensor array with a Laue diffraction pattern formed thereon.

Referring now to FIGS. 2 through 4 of the drawings, an angle detector device according to an embodiment of this invention for detecting the angular position or orientation of a silicon wafer is described. The angle detector device determines the angular position of the wafer for the adjustment of the orientation thereof in a photolithography exposure step by means of X-rays.

Figure 1:
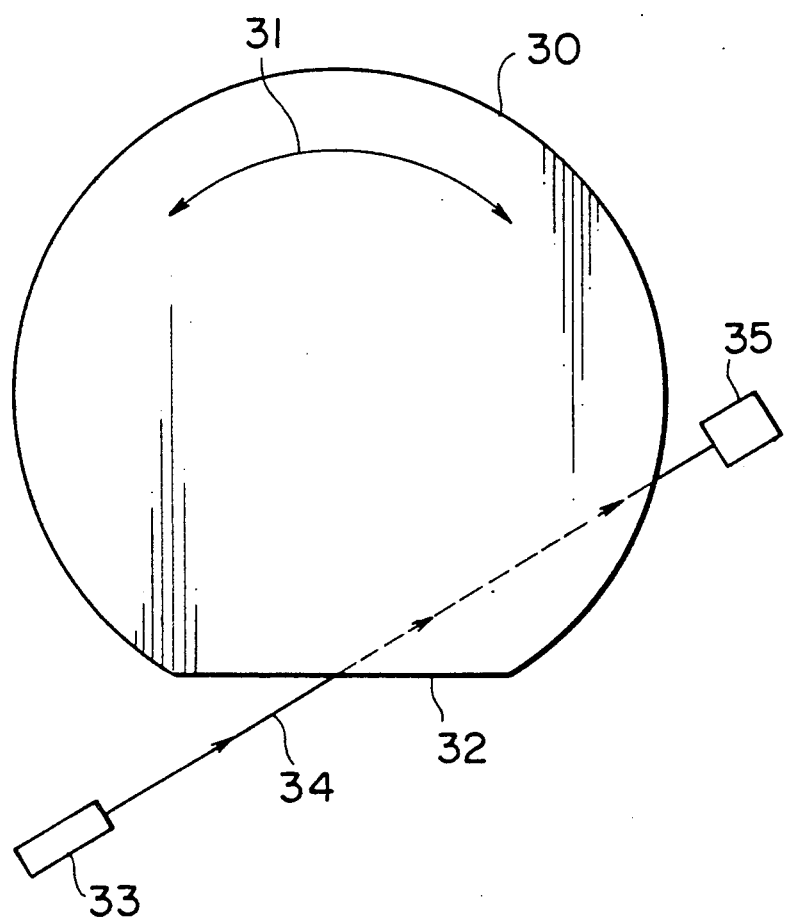
FIG. 1 is a schematic view of a conventional angle detector device for silicon wafers.

As shown in FIG. 2, the silicon wafer 30 having an orientational flat 32 as described above by reference to FIG. 1 is supported on a goniometer (not shown) for adjusting the angular position or orientation of the wafer 30 both with respect to the rotational position of the wafer 30 around its central axis and with respect to the direction of the main surface of the wafer 30. The wafer 30 has a photoresist formed on the main front surface thereof (at the left side in FIG. 2) which is to be exposed by an X-ray beam 11 generated by a synchrotron 10. The exposure of the wafer 30 is effected in the subsequent photolithography step. The synchrotron 10 also serves as an X-ray source for generating an X-ray beam 12 for the determination of the angular position of the silicon wafer 30. Thus, the X-ray generated by the synchrotron 10 is divided into two portions: an X-ray beam 11 for exposing the photoresist formed on a main surface of the wafer 30, and an X-ray beam 12 for determining the angular position of the wafer 30. The angle detector device according to this invention comprises, in addition to the synchrotron 10 as its X-ray source, a pair of monocrystalline silicon plates 13a and 13b serving as diffraction gratings, a slit 14 having a pin-hole for collimating the X-ray beam 12, a two-dimensional photosensor array 15, and an angle determination means coupled to the output of the photosensor array 15, as described in detail below.

The determination of the angular position of the wafer 30 is effected by the angle detector device as follows. First, an approximate angular position of the wafer 30 is determined utilizing the orientational flat 32 as described above in reference to FIG. 1. Then, as shown in FIG. 2, the X-ray beam 12 for angle determination generated by the synchrotron 10 is reflected by a pair of monocrystalline silicon plates 13a and 13b and directed, via a slit 14 and a central hole 15a in the two-dimensional photosensor array 15, onto a central portion of the back surface of the wafer 30 opposite to the main surface thereof on which the photoresist which is to be exposed in the subsequent exposure step is formed. Thus, the photoresist on the wafer 30 remains unexposed during this angle determination. The X-ray beams 16 diffracted at the wafer 17 fall on the two-dimensional photosensor array 15 to form a back Laue diffraction pattern thereon.

The Laue diffraction pattern formed on the photosensor array 15 has a configuration which is characteristic of the orientation of the wafer 30 as well as the crystal structure thereof. FIG. 3 shows in a diagramatic perspective view the Laue diffraction pattern (as viewed from the back side) which is formed on the photosensor array 15 in the case where the main surface of the wafer 30 corresponds to a (111) plane of a crystalline silicon wafer. Thus, the diffraction pattern comprises spots 20 through 26 having a six-fold symmetry around the center, i.e., the pattern 20 through 26 is invarient under a rotation of $2\pi/6$ around the center. (In the case where the main surface of the silicon wafer 30 is a (100) crystal plane, the Laue diffraction pattern has a four-fold symmetry around the center and hence is invariant under a rotation of $2\pi/4$.)

When the angular position or orientation of the silicon wafer 30 deviates from the predetermined position, this deviation of the orientation of the wafer 30 appears in the Laue diffraction pattern formed on the photosensor array 15. Namely, when the rotational position of the disk-shaped wafer 30 around its central axis deviates by an angle $\theta$ from the predetermined position, then the diffraction pattern 20 through 25 is also rotated around its center by the same angle $\theta$ with respect to the normal positions thereof as represented in FIG. 3. Thus, in the case shown in FIG. 3, the rotational position of the wafer 30 around its central axis can be determined, for example, from the positions of the spots 20 and 21 on the photosensor array 15. On the other hand, when the direction of the main surface of the wafer 30 is deviated from the predetermined direction, such deviation results in an asymmetry of the Laue pattern 20 through 25 with respect to its center. Thus, in the case shown in FIG. 3, the deviation of the orientation of the main surface of the wafer 30 in the horizontal rotational direction can be determined from the observation of the positions of the spots 22 through 25.

FIG. 4 shows an example of the implementation of the angle determination means 40 for effecting the determination of the angular position or orientation of the wafer 30 according to the above principle. The angle determination means 40 comprises image processing means 40a, memory means 40b, and calculation means 40c. The output signal S of the photosensor array 15 is processed by the image processor 40a to obtain an output A corresponding to the Laue pattern 20 through 25 formed on and detected by the sensor array 15. On the other hand, the memory means 40 stores the information B corresponding to the Laue pattern which is to be formed on the photosensor array 15 when the wafer 30 is at the predetermined angular position where the crystal axes of the wafer 30 are precisely aligned with the exposure device. On the basis of the information A and B received from the image processor 40a and the memory 40b, the calculation means 40c determines the deviation of the detected Laue pattern from that stored in the memory 40b, and generates an output signal C corresponding to the angular position of the wafer 30.

The advantages of the angle detector device according to this invention are as follows. First, since the directions of the crystal axes of the wafer can be determined directly, precise orientation of the wafer becomes possible. Further, since the adjustment of the angular position of the wafer 30 can be effected while the wafer 30 is mounted on the wafer stage on which the wafer 30 is exposed in the subsequent photolithography step, the setting precision of the wafer is not reduced by intervening movements of the wafer 30 which otherwise take place after the angular position thereof is set. The angle detector device according to this invention is thus especially suited for the determination and adjustment of the angular position of silicon wafers before the exposure thereof in the production of quantum-effect semiconductor devices.

While description has been made of the particular embodiment of this invention, it will be understood that many modifications may be made without departing from the spirit thereof. For example, although a synchrotron was utilized as the X-ray source in the above embodiment, other X-ray sources may be used as well. Further, the silicon plates 13a and 13b may be replaced by other types of mirrors. Furthermore, although the angle determination is effected by means of an X-ray beam incident on the back surface of the wafer, an X-ray beam incident on a portion of the front surface on which semiconductor device chips are not formed may be utilized as well for the angle determination. The appended claims are contemplated to cover any such modifications as fall within the true spirit and scope of this invention.

What is claimed is:

1. An angle detecting device for detecting the angular position of a crystalline semiconductor wafer, comprising:

X-ray irradiation means for generating an X-ray beam directed onto a wafer for diffraction thereby;

two-dimensional array sensor means for detecting a Laue diffraction pattern formed by diffraction of the X-ray beam by the wafer; and angle determination means, coupled to the output of said sensor means, for determining the angular position of the wafer in response to the Laue diffraction pattern detected by said sensor means.

2. The angle detecting device as claimed in claim 1 wherein:

said sensor means comprises a two-dimensional photosensor array for detecting the Laue diffraction pattern; and said angle determination means comprises image processing means, coupled to said photosensor array, for generating an output signal corresponding to the detected Laue diffraction pattern; memory means for storing a Laue diffraction pattern corresponding to a predetermined angular position of the wafer; and calcualtion means, coupled to the image processing means and the memory means, for determining deviation of the detected Laue diffraction pattern from the stored Laue diffraction pattern, the calculation means thereby determining the angular position of the wafer with respect to crystal axes thereof.

3. The angle detecting device as claimed in claim 1 wherein said wafer comprises a silicon wafer.

4. The angle detecting device as claimed in claim 1 wherein said X-ray irradiation means comprises an X-ray source for exposing the wafer in a photolithography step.

5. The angle detecting device as claimed in claim 1 wherein the X-ray irradiation means generates an X-ray beam for exposing a resist disposed on a front surface of a crystalline wafer and for irradiating a rear surface, opposed to the front surface, of the crystalline wafer to determine crystalline orientation of the wafer and further comprising:

means for supporting the crystalline wafer with the front surface disposed directly opposite the X-ray irradiation means; and means for reflecting the X-ray beam to irradiate the rear surface of the crystalline wafer, wherein the means for supporting is disposed between the X-ray radiation means and the means for reflecting and the sensor means is disposed between the means for supporting and means for reflecting for detecting a Laue diffraction pattern formed by diffraction of the X-ray beam from the rear surface of the wafer.

6. The angle detecting device as claimed in claim 5 wherein said means for reflecting comprises a pair of crystalline silicon plates.

7. The angle detecing device as claimed in claim 2 wherein said photosensor array includes a pinhole for passage of the X-ray beam from the means for reflecting to the rear surface of the crystalline wafer.

* * * * *